United States Patent
Han et al.

(10) Patent No.: US 8,109,138 B2
(45) Date of Patent: Feb. 7, 2012

(54) METHOD AND SYSTEM FOR ESTIMATING ENGINE OIL LIFE BASED ON VISCOSITY

(75) Inventors: Taeyoung Han, Bloomfield Hills, MI (US); Liyun Zheng, Troy, MI (US)

(73) Assignee: GM Global Technology Operations LLC

( * ) Notice: Subject to any disclaimer, the term of this patent is extended or adjusted under 35 U.S.C. 154(b) by 612 days.

(21) Appl. No.: 12/273,733

(22) Filed: Nov. 19, 2008

(65) Prior Publication Data

US 2010/0122571 A1 May 20, 2010

(51) Int. Cl.
G01M 15/00 (2006.01)
G01M 11/00 (2006.01)

(52) U.S. Cl. ..................... 73/114.55; 73/53.05
(58) Field of Classification Search .................. 73/53.05, 73/54.01, 54.02, 54.16, 114.55
See application file for complete search history.

(56) References Cited

U.S. PATENT DOCUMENTS

| | | | | |
|---|---|---|---|---|
| 5,968,371 A | * | 10/1999 | Verdegan et al. | 210/739 |
| 6,216,528 B1 | * | 4/2001 | Carrell et al. | 73/54.01 |
| 6,286,360 B1 | * | 9/2001 | Drzewiecki | 73/24.01 |
| 6,415,652 B1 | * | 7/2002 | Carrell et al. | 73/54.02 |
| 6,508,107 B2 | * | 1/2003 | Carrell et al. | 73/54.02 |
| 6,553,812 B2 | * | 4/2003 | Park et al. | 73/54.01 |
| 6,895,807 B2 | * | 5/2005 | Han et al. | 73/53.05 |
| 6,901,788 B2 | * | 6/2005 | Han et al. | 73/53.05 |
| 7,259,664 B1 | * | 8/2007 | Cho et al. | 340/450.2 |
| 7,281,414 B2 | * | 10/2007 | Cho | 73/54.24 |
| 2002/0011095 A1 | * | 1/2002 | Park et al. | 73/54.01 |
| 2002/0083758 A1 | * | 7/2002 | Carrell et al. | 73/54.02 |
| 2004/0211246 A1 | * | 10/2004 | Han et al. | 73/53.05 |
| 2005/0039521 A1 | * | 2/2005 | Han et al. | 73/53.05 |
| 2006/0114007 A1 | * | 6/2006 | Cho | 324/698 |
| 2008/0289400 A1 | * | 11/2008 | Quist et al. | 73/54.01 |

FOREIGN PATENT DOCUMENTS

| | | | |
|---|---|---|---|
| CN | 1807850 A | | 7/2006 |
| JP | 05010866 A | * | 1/1993 |

* cited by examiner

Primary Examiner — John Fitzgerald

(57) ABSTRACT

A method and control module for indicating engine oil life includes a viscosity determination module determining a viscosity of the engine oil based on an engine oil pressure and engine oil temperature. The control system further includes a comparison module comparing the viscosity of the engine oil to a threshold and generating a warning signal in response to comparing the viscosity.

20 Claims, 7 Drawing Sheets

METHOD AND SYSTEM FOR ESTIMATING ENGINE OIL LIFE BASED ON VISCOSITY

FIELD

The present disclosure relates to vehicle control systems and more particularly to a system and method for estimating engine oil life based on viscosity.

BACKGROUND

This section provides background information related to the present disclosure which is not necessarily prior art. The background information provided herein is for the purpose of generally presenting the context of the disclosure. Work of the presently named inventors, to the extent it is described in this background section, as well as aspects of the description that may not otherwise qualify as prior art at the time of filing, are neither expressly nor impliedly admitted as prior art against the present disclosure.

Motorized vehicles may include a powertrain that includes a powerplant (e.g., an engine, an electric motor, and/or a combination thereof), a multispeed transmission, and a differential or final drive train. The powerplant may include an engine that produces drive torque that is transmitted through one of various gear ratios of the transmission to the final drive train to drive wheels of the vehicle.

Engine oil is used to lubricate the components in the engine. Engine oil deteriorates with use. Engine oil must therefore be replaced. Traditionally, engine oil was changed whenever the vehicle reached a predetermined mileage, or a specified duration, which ever comes first. Under severe operating conditions, however, vehicle manufacturers may suggest that the engine oil be changed more frequently. These situations require the operator of the vehicle to make a judgment as to when to change the engine oil. Other manufacturers provide a system for determining engine oil life. One example of an engine oil life system is the General Motors (GM) Engine Oil Life System (EOLS). EOLS keeps track of the various operating conditions of the vehicle and adjusts the mileage between oil changes. EOLS is responsible for determining the percentage remaining life of the engine oil and whether the engine oil needs to be changed. Excessive degradation of the engine oil occurs at its temperature extremes. At high oil temperatures, antioxidants in the oil tend to become depleted, and the oil becomes more viscous and acidic due to oxidation. At low oil temperatures, fuel, water and soot tend to accumulate in the oil, reducing its viscosity and increasing wear. Letting a driver to take into consideration these conditions is not practical. Even with these factors, certain conditions are not considered.

SUMMARY

The present disclosure increase provides a system and method for increasing the accuracy of predicting oil life between the oil change indicators. The present disclosure uses viscosity to improve the oil life indication. Too high oil viscosity will result in too high oil pressure build up and hampers sufficient oil flow to supply fresh lubricant to critical areas of the engine, and accelerated wear will result. Too low oil viscosity will results in poor hydrodynamic lubrication of the loaded surfaces. Therefore, the "viscosity of oil" improves the oil life determination.

In one aspect of the disclosure, a method includes determining an engine oil pressure, determining an engine oil temperature, determining a viscosity of the engine oil based on the engine oil pressure and engine oil temperature, comparing the viscosity of the engine oil to a threshold, and generating a warning signal in response to comparing the viscosity.

In another aspect of the disclosure, a method includes determining a new oil viscosity, determining a used oil viscosity, when a ratio of a used oil viscosity and the new oil viscosity is outside a range, generating an indicator corresponding to oil life.

In a further aspect of the disclosure, a control module for indicating engine oil life includes a viscosity determination module determining a viscosity of the engine oil based on n engine oil pressure and engine oil temperature. The control system further includes a comparison module comparing the viscosity of the engine oil to a threshold and generating a warning signal in response to comparing the viscosity.

Further areas of applicability of the present disclosure will become apparent from the detailed description provided hereinafter. It should be understood that the detailed description and specific examples, while indicating the preferred embodiment of the disclosure, are intended for purposes of illustration only and are not intended to limit the scope of the disclosure.

BRIEF DESCRIPTION OF THE DRAWINGS

The present disclosure will become more fully understood from the detailed description and the accompanying drawings, wherein.

DETAILED DESCRIPTION OF THE PREFERRED EMBODIMENTS

The following description of the preferred embodiment is merely exemplary in nature and is in no way intended to limit the disclosure, its application, or uses. As used herein, the term module refers to an application specific integrated circuit (ASIC), an electronic circuit, a processor (shared, dedicated, or group) and memory that execute one or more software or firmware programs, a combinational logic circuit, and/or other suitable components that provide the described functionality.

Figure 1:
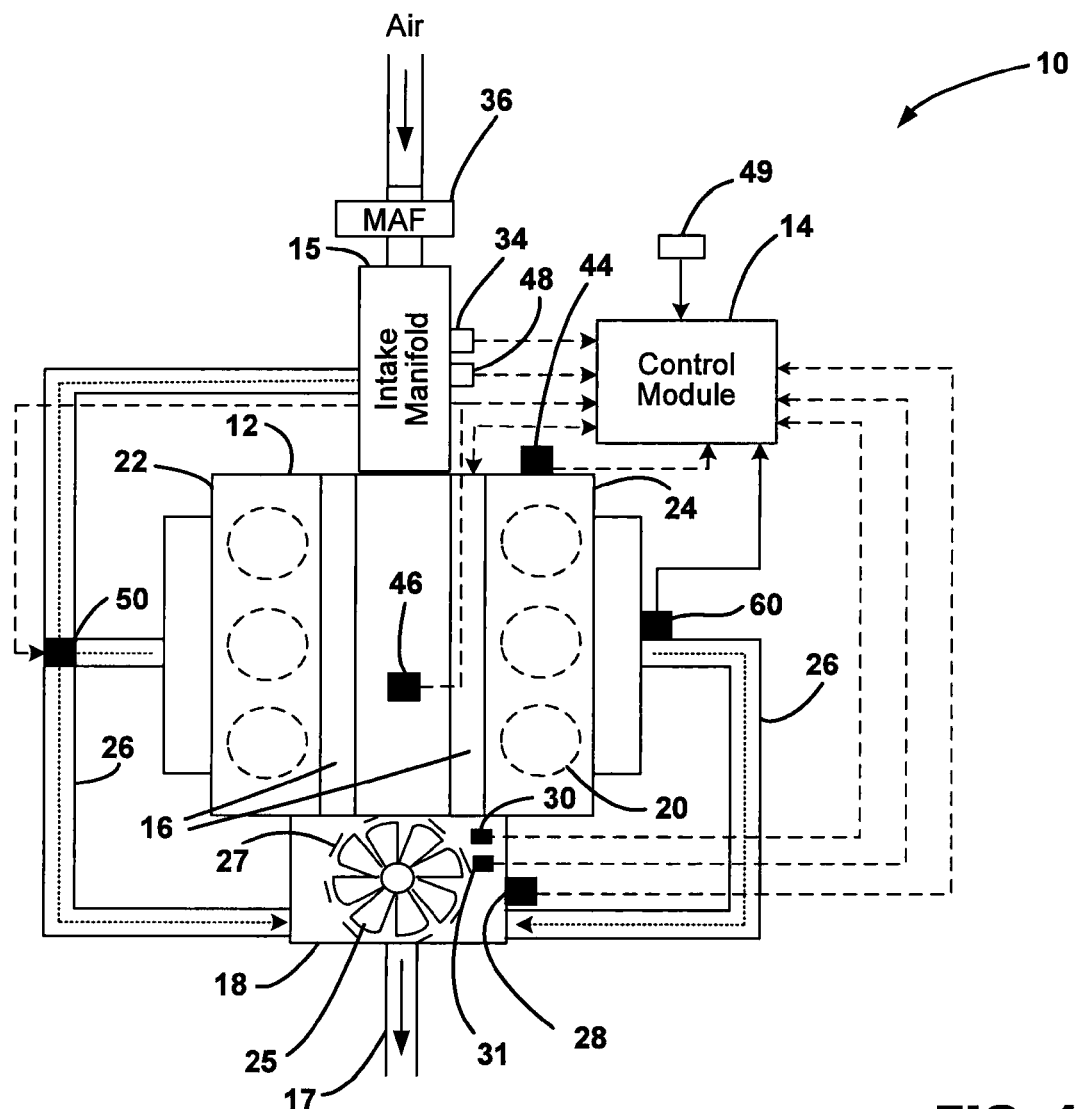
FIG. 1 is a functional block diagram of an engine and engine control system.

Referring now to FIG. 1, an exemplary engine control system 10 is schematically illustrated in accordance with the present disclosure. The engine control system 10 includes an engine 12 and a control module 14. The engine 12 includes an intake manifold 15, a fuel injection system 16 having fuel injectors and an exhaust system 17. The system 10 may also include a turbocharger 18. The exemplary engine 12 includes six cylinders 20 configured in adjacent cylinder banks 22, 24 in a V-type layout. Although FIG. 1 depicts six cylinders (N=6), it can be appreciated that the engine 12 may include additional or fewer cylinders 20. For example, engines having 2, 4, 5, 8, 10, 12 and 16 cylinders are contemplated. It is also anticipated that the engine 12 can have an inline-type cylinder configuration. While a gasoline powered internal combustion engine utilizing direct injection is contemplated, the disclosure may also apply to diesel or alternative fuel sources.

During engine operation, air is drawn into the intake manifold 15 by the inlet vacuum created by the engine intake stroke. Air is drawn into the individual cylinders 20 from the intake manifold 15 and is compressed therein. Fuel is injected by the injection system 16. The air/fuel mixture is compressed and the heat of compression and/or electrical energy ignites the air/fuel mixture. Exhaust gas is exhausted from the cylinders 20 through exhaust conduits 26. The exhaust gas drives the turbine blades 25 of the turbocharger 18 which in turn drives compressor blades 25. The compressor blades 25 can deliver additional air (boost) to the intake manifold 15 and into the cylinders 20 for combustion.

The turbocharger 18 can be any suitable turbocharger such as, but not limited to, a variable nozzle turbocharger (VNT). The turbocharger 18 can include a plurality of variable position vanes 27 that regulate the amount of air delivered from the vehicle exhaust 17 to the engine 12 based on a signal from the control module 14. More specifically, the vanes 27 are movable between a fully-open position and a fully-closed position. When the vanes 27 are in the fully-closed position, the turbocharger 18 delivers a maximum amount of air into the intake manifold 15 and consequently into the engine 12. When the vanes 27 are in the fully-open position, the turbocharger 18 delivers a minimum amount of air into the engine 12. The amount of delivered air is regulated by selectively positioning the vanes 27 between the fully-open and fully-closed positions.

The turbocharger 18 includes an electronic control vane solenoid 28 that manipulates a flow of hydraulic fluid to a vane actuator (not shown). The vane actuator controls the position of the vanes 27. A vane position sensor 30 generates a vane position signal based on the physical position of the vanes 27. A boost sensor 31 generates a boost signal based on the additional air delivered to the intake manifold 15 by the turbocharger 18. While the turbocharger implemented herein is described as a VNT, it is contemplated that other turbochargers employing different electronic control methods may be employed.

A manifold absolute pressure (MAP) sensor 34 is located on the intake manifold 15 and provides a (MAP) signal based on the pressure in the intake manifold 15. A mass air flow (MAF) sensor 36 is located within an air inlet and provides a mass air flow (MAF) signal based on the mass of air flowing into the intake manifold 15. The control module 14 uses the MAF signal to determine the A/F ratio supplied to the engine 12. An RPM sensor 44 such as a crankshaft position sensor provides an engine speed signal. An intake manifold temperature sensor 46 generates an intake air temperature signal. The control module 14 communicates an injector timing signal to the injection system 16. A vehicle speed sensor 49 generates a vehicle speed signal.

The exhaust conduits 26 can include an exhaust recirculation (EGR) valve 50. The EGR valve 50 can recirculate a portion of the exhaust. The controller 14 can control the EGR valve 50 to achieve a desired EGR rate.

The control module 14 controls overall operation of the engine system 10. More specifically, the control module 14 controls engine system operation based on various parameters including, but not limited to, driver input, stability control and the like. The control module 14 can be provided as an Engine Control Module (ECM).

The control module 14 can also regulate operation of the turbocharger 18 by regulating current to the vane solenoid 28. The control module 14 can communicate with the vane solenoid 28 to provide an increased flow of air (boost) into the intake manifold 15.

An exhaust gas oxygen sensor 60 may be placed within the exhaust manifold or exhaust conduit to provide a signal corresponding to the amount of oxygen in the exhaust gasses.

Figure 2:
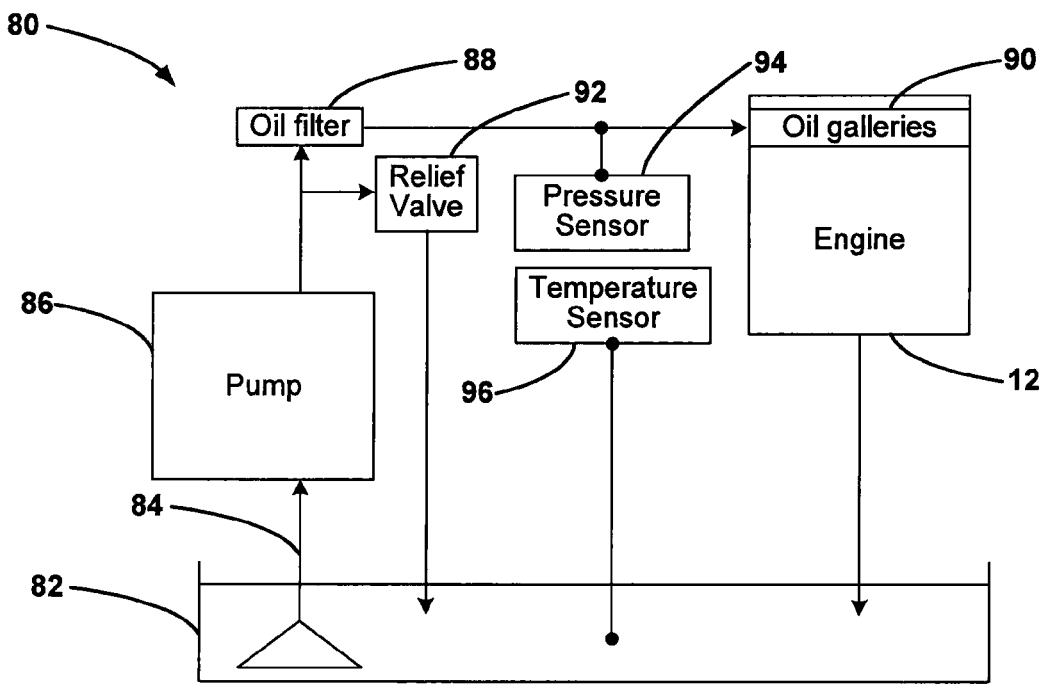
FIG. 2 is a functional block diagrammatic view of an oil lubricating system for the engine of FIG. 1.

Referring now to FIG. 2, a block diagrammatic view of an engine oiling system 80 is illustrated. The engine oiling system 80 includes an oil sump 82 that is typically located at the bottom of the engine. An engine oil pick-up tube 84 draws oil therein due to the action of a pump 86. The pump 86 draws oil from the sump 82 through the pick-up tube 84 and into an oil filter 88. The oil filter 88 provides fluid to oil galleries 90 for lubricating various portions of the engine 12 including the bearings, pistons, rods and other internal components of engine 12. From the galleries 90 the oil returns to the sump 82.

The pump 86 may be different types of pump including a gear-type positive displacement pump or a vane-type variable displacement pump. For a displacement pump, a relief valve 92 is used to recirculate the excessive oil outside of the hot idling operation. The waste oil recirculating through the relief valve 92 may ultimately reduce the overall fuel economy of the vehicle since an excessive amount of energy is used to drive the positive displacement pump.

A pressure sensor 94 in communication with the oil between the oil filter 88 and the oil galleries 90 generates an oil pressure signal. A temperature sensor 96 in communication with the oil in the sump provides an engine oil temperature signal.

The engine oil pressure is caused by the resistance of the oil to flow under the pumping action of the oil pump. The higher the oil viscosity, the higher the resistance to oil flow. The oil pressure is a measure of the oil's resistance to flow. The oil pressure in the engine oiling system is a function of two factors: oil viscosity and oil flow rate. Most current engines today are a positive displacement type.

The pump 86 may also be a variable displacement lubricating oil pump used to minimize the waste of oil recirculation due to inherent capability of delivering right amount of oil flow at various operating conditions.

The oil flows in an engine may be unregulated until a certain flow, then regulated thereafter. For both positive and variable displacement type pumps, in general, the oil flow rates are proportional to the speed (RPM) of the oil pump when the oil flow is not regulated. The oil pumps are directly coupled with engine speed and the speed of the oil pump directly relates with the engine RPM. Therefore, for a given engine speed (RPM) such as at idle, the oil flow rate is nearly constant and the oil pressure is mainly a function of oil viscosity. However, the oil viscosity is sensitive to temperature of the oil. The viscosity of oil decreases as the temperature of the oil increases. Since the oil viscosity is the driving force to resist flow, the oil pressure tends to decreases as the oil temperature increases. Conversely, as the oil temperature decreases, oil pressure in the oiling system increases. Therefore, by measuring the oil pressure and the oil temperature, a relationship between the oil viscosity and the oil pressure can be built.

For regulated oil flow, the pump tries to maintain preset pressure at its outlet by adjusting its delivery flow in accordance with the system requirements. If pressure differential across the pump is less than the setting pressure, the pump outputs its maximum delivery corrected for internal leakage. After the pressure setting has been reached, the output flow is regulated to maintain preset pressure by changing the pump's displacement. The displacement can be changed from its maximum value down to zero, depending upon the downstream oil pressure. The pressure range between the preset pressure and the maximum pressure, at which the displacement is zero, is referred to as a regulation range. From the pump characteristics including the relationship between the displacement and the oil pressure, the oil flow rates can be determined even in the oil regulation range.

As the volume of oil pumped into the engine increases, the oil pressure increases. Oil pressure is a function of two factors for a given engine: oil viscosity and oil flow rate. The oil flow in oil galleries is typically laminar. For laminar flow in a channel, the total pressure drop, $\Delta P$, is linearly proportional to the product of the oil flow rate, Q, and the oil viscosity, $\mu$ $$\Delta P \approx Q \times \mu \tag{1}$$

From Eqn. (1), the oil viscosity, $\mu$, becomes $$\mu \approx \frac{\Delta P}{Q} \tag{2}$$

The oil flow rate, Q, is a function of engine RPM, $\omega$, and oil flow regulation.

For an unregulated oil flow, most oil pumps behave as a positive displacement pump. The oil flow rate of such positive displacement pumps is proportional to the rotational speed (RPM) of the oil pump. Since the oil pump speed is directly proportional to engine speed, $\omega$, the oil viscosity, $\mu$, is simply a function of oil pressure and engine RPM, $\omega$, $$\mu \approx \frac{\Delta P}{\omega} \tag{3}$$

For regulated oil flow, the oil flow rate, Q, depends on both engine RPM and the oil pressure. The oil flow rate, Q, to engine gallery in Eqn. (2) has to be modified by the amount of the regulated oil flow rate. The amount of regulation depends on an oil pump characteristics of a particular pump type. The regulated oil flow rate can be approximated by modeling the regulated oil flow rate, f, as a function of oil pressure and engine RPM, $$Q \approx Q_{unregulated} - f(\Delta P, \omega) \tag{4}$$

Once the oil pump characteristics are known, such as the relationship between the regulated oil flow rate and the oil pressure, and the pump speed, Eqn. (2) can be applied to wide range of engine operating conditions beyond unregulated region.

Figure 3:
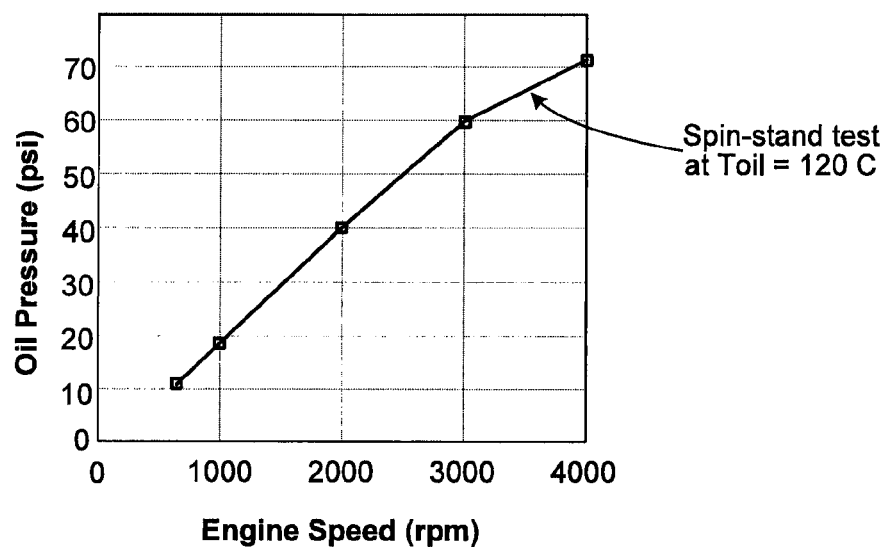
FIG. 3 is a plot oil pressure versus engine speed at a constant temperature.
Figure 4:
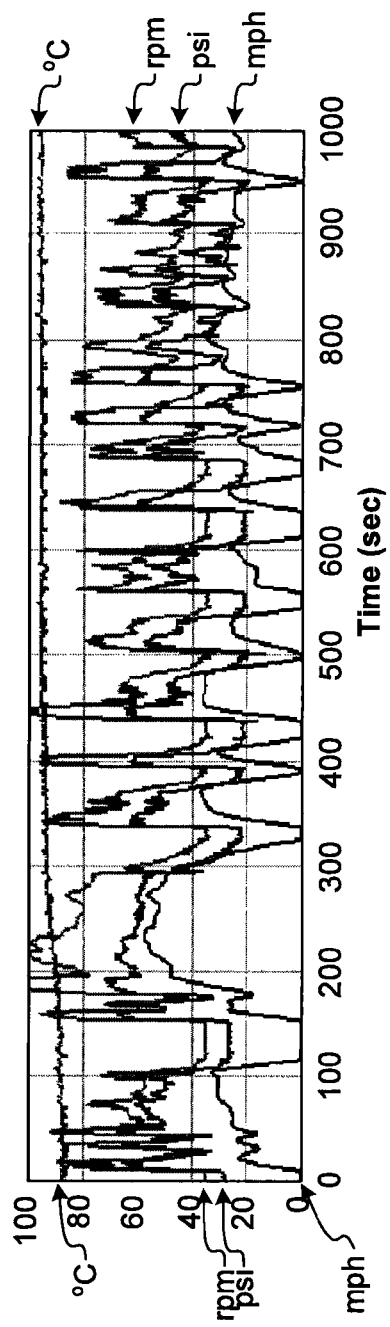
FIG. 4 is a plot of vehicle speed, oil pressure, oil temperature, engine speed for a test engine.
Figure 5:
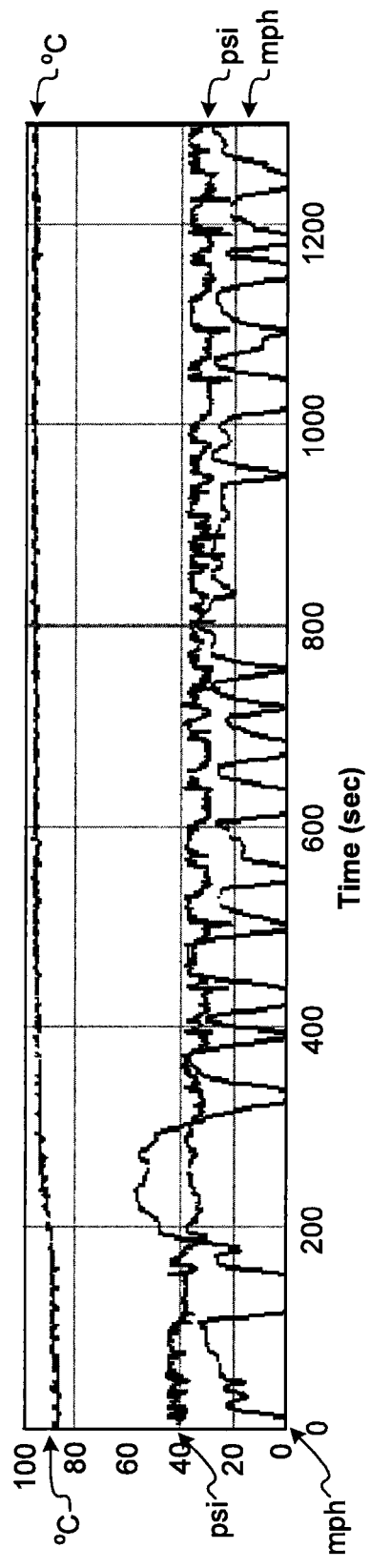
FIG. 5 is a plot of vehicle speed, oil temperature and oil viscosity index versus time.
Figure 6:
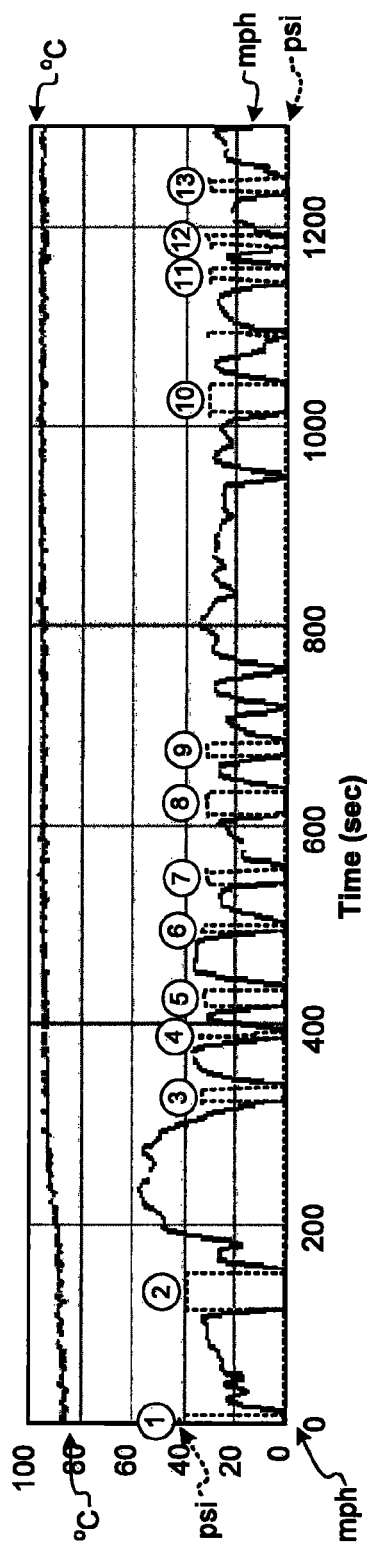
FIG. 6 is a plot of engine speed, oil temperature and viscosity index at idle during a test cycle.
Figure 7:
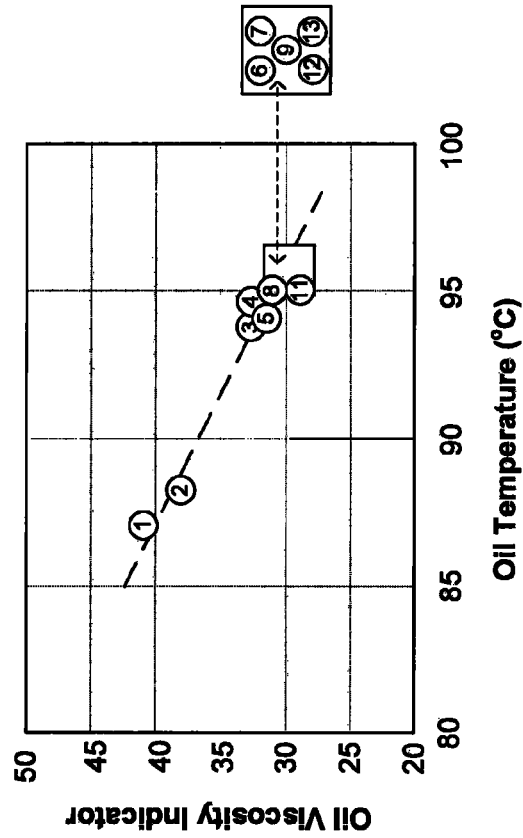
FIG. 7 is a plot of an oil viscosity indicator versus the oil temperature during a driving cycle.

Referring now to FIG. 3, to validate Eqn. (3), a spin-stand test data using a GM 4.2 L, L6 engine were used to plot the relationship between the oil pressure and the engine RPM at a constant oil temperature 120° C. As shown in FIG. 2, the oil pressure increases linearly with the engine RPM until the relief valve starts open near the oil pressure 60 psi. Higher oil pressures above 60 psi, the oil flow starts to regulate through the relief valve and the oil pressure deviates from the linear relationship. In order to apply to more realistic engine operating conditions, the engine chassis dynamometer was operated using the Federal Test Procedure (FTP) test for city driving cycle. FIG. 4 shows the variations of the vehicle speed, engine RPM and also corresponding oil pressure fluctuations and the oil temperature variations in the oil sump. As shown in FIG. 5, the oil pressure fluctuates largely due to engine RPM variation during the acceleration and the deceleration. FIG. 5 shows the oil viscosity indicator which is the oil pressure divided by the engine RPM from Eqn. (3) as signal 110. The oil viscosity indicator is fluctuating during FTP cycle as the oil flow is regulated through the relief valve at high engine RPM and the oil flow circuit in engine galleries varies due to variable valve actuations. To avoid these complexities, only the data during idle conditions were utilized as the oil flow circuit is steady and not regulated. As shown in FIG. 6, the oil viscosity indicator values are vary stable and does not fluctuate during the engine idle speed. The averages values of the oil viscosity indicator at 13 idle conditions were plotted as a function of oil temperature in FIG. 7. The 13 data points for the oil viscosity indicator falls closely along the linear relationship between the oil viscosity and the oil temperature for the narrow oil temperature range available in the test between 85° C. and 95° C.

Figure 8:
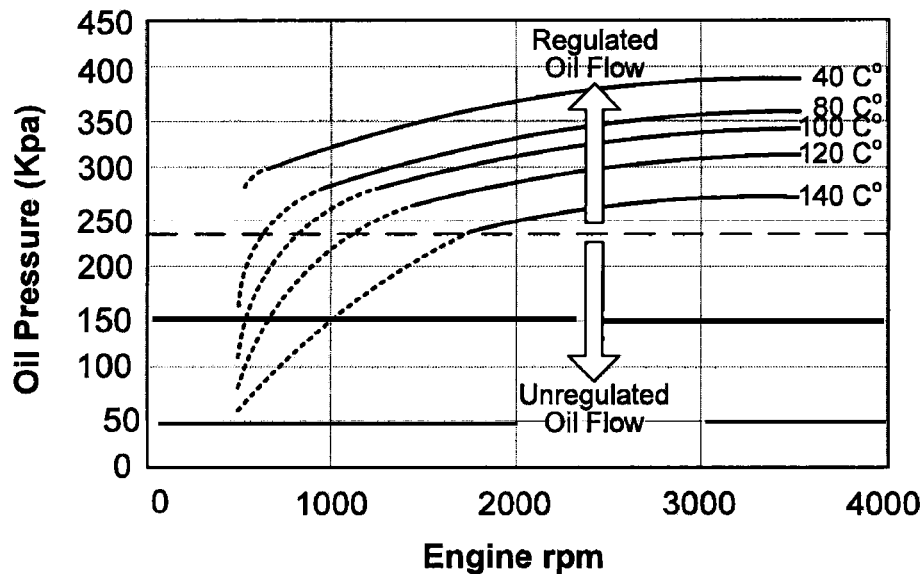
FIG. 8 is a plot of oil pressure versus engine speed at different oil temperatures.
Figure 9:
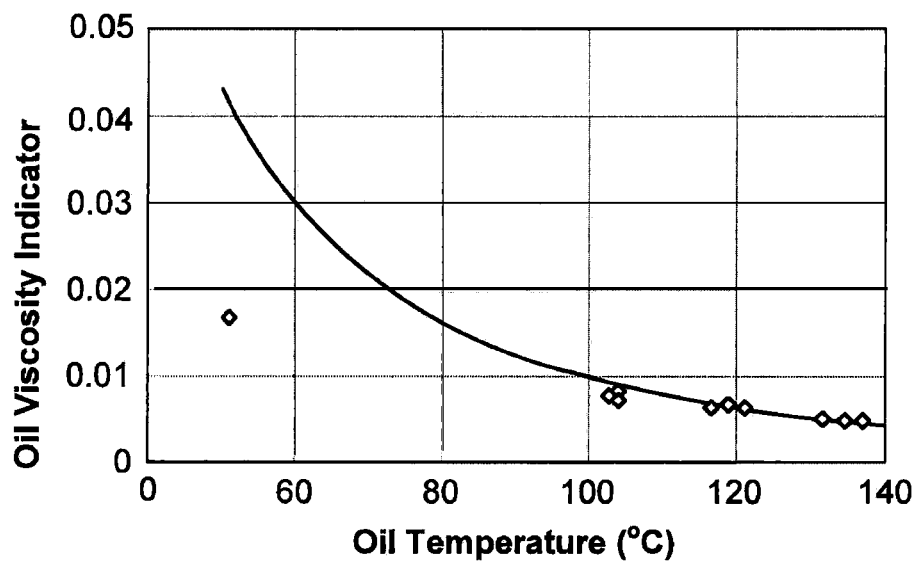
FIG. 9 is a plot of oil viscosity versus oil temperature for an engine below 800 RPM's of crankshaft speed.

In order to apply the present invention to variable displacement pumps, a GM LT8, Gamma engine was utilized. The relationship between the oil pressure and the engine RPM is shown in FIG. 8 at five different oil temperatures. For oil pressures below 230 Kpa, the oil flow is not regulated. The oil flow starts to regulate when the oil pressure is higher than 230 Kpa. As shown in FIG. 8, the relationship between the oil pressure and the engine RPM is linear for the unregulated oil flow region when the oil pressure is below 230 Kpa and the data deviates from a linear relationship when the oil pressure is greater than 230 Kpa. Therefore, Eqn. (3) can still be applied to a variable displacement pump when the oil flow is not regulated. The engine test data at low engine RPM's (below 810) were selected to evaluate the oil viscosity indicator based on Eqn. (3). The averaged values of these engine test data were plotted as a function of the oil temperature, as shown in FIG. 9. Although the test data for 50° C. oil temperature in the plot is included, the oil flow is already regulated at this low oil temperature and this data point is not valid to estimate the oil viscosity. As shown in FIG. 9, the oil viscosity indicator values from Eqn. (3) are scaled with a constant, k2, to compare directly with the viscosity values of 5W30 engine oil. The scaled oil viscosity from Eqn. (3) falls very closely with the measured oil viscosity. However, as expected, it deviates from the measured oil viscosity at a low oil temperature, 50° C., as the oil flow is regulated. In order to determine viscosity in a regulated region, Eqn. (2) is used with Eqn. (4) to take into account the corrected amount of oil flow.

Figure 10:
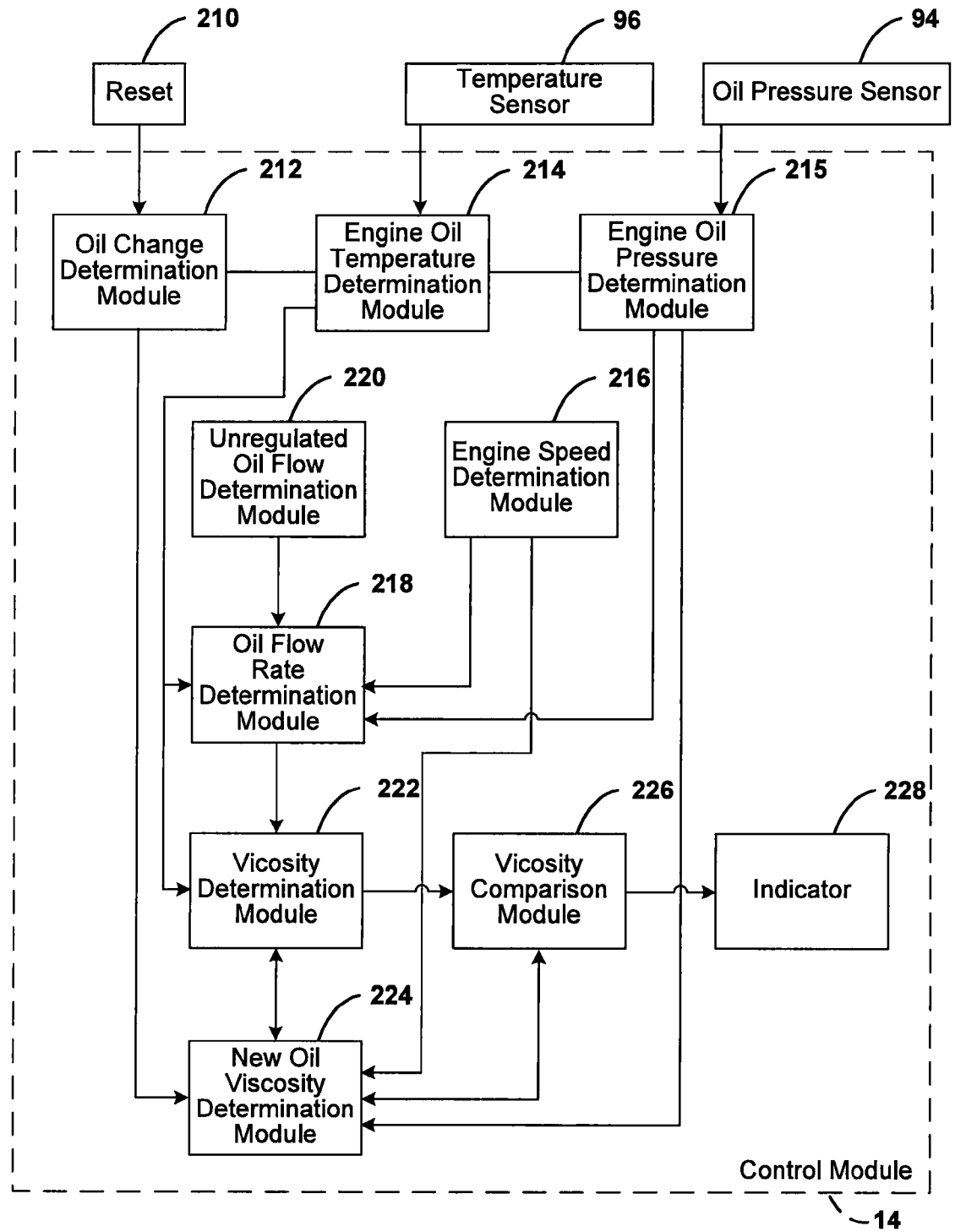
FIG. 10 is a block diagram of the control system of FIG. 1 for performing the method of the present disclosure.

Referring now to FIG. 10, a simplified block diagrammatic view of the components of the control module 14 for engine oil monitoring is illustrated. Each of the modules within the control module 14 may be interconnected. The control module 14 may include various modules therein to perform the method of the present disclosure.

The control module 14 may be in communication with a reset 210. The reset 210 may be a reset switch or other type of reset interface. A reset switch may, for example, be located on the instrument panel. The reset switch may be a combination of switches that are activated in a certain sequence to generate a signal as an indicator that the oil has been changed in the vehicle.

The control module 14 may include an oil change determination module 212 that receives the reset signal from the reset 210.

An engine oil temperature determination module 214 receives a temperature signal from the temperature sensor 96 and provides the temperature signal to various other modules within the control module 14. An engine oil pressure determination module 215 receives an oil pressure sensor signal from the oil pressure sensor 94 and provides the oil pressure signal to other modules within the control module 14. An engine speed determination module 216 provides an engine speed signal to the oil flow rate determination module 218. The oil flow rate determination module 218 may also receive a signal from the unregulated oil flow determination module 220. Based on the oil flow rate signal generated at the oil flow rate determination module 218, a viscosity signal may be generated by a viscosity determination module 222. The viscosity determination module 222 may determine the viscosity and correlate the viscosity with the temperature. The viscosity determination module output may store a new oil viscosity in a memory 224. Thus, when the reset switch is first reset, the engine oil is new and thus a new oil viscosity determination is made and stored in the new oil viscosity memory 224.

The viscosity determination module 222 may also be in communication with a viscosity comparison module 226. The viscosity comparison module may compare the new oil viscosity and the viscosity of the used oil from the viscosity determination module 222. By comparing the ratio of the used viscosity and new viscosity to a threshold, an indicator 228 may be used to indicate whether or not an oil change is required. The viscosity comparison module 226 may compare an upper constant and a lower constant to the ratio of the used viscosity and new viscosity. When the viscosity is between the two constants, the viscosity is within range and the indicator 228 is not activated. When the viscosity is either above or below the outer constant, the viscosity comparison module 226 may activate the indicator 228. The indicator 228 may provide an indication that an oil change is due or that the oil has an amount of predetermined life. Of course, having two constants is merely one example provided by the present disclosure. A variation of the present disclosure may use only one constant.

Figure 11:
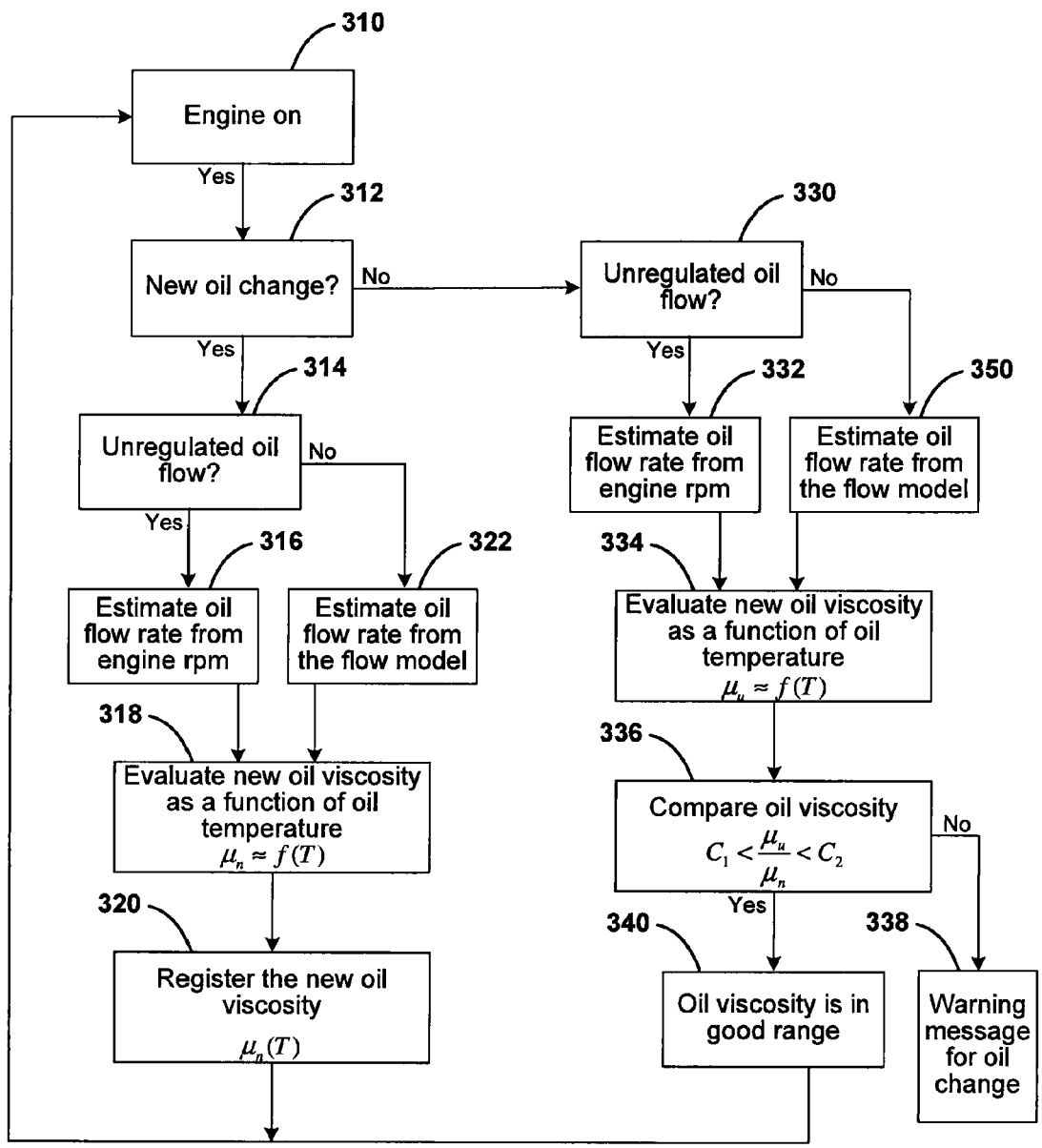
FIG. 11 is a flowchart of a method for performing the present disclosure.

Referring now to FIG. 11, a method of controlling an engine around an intrusive diagnostic procedure is set forth. As mentioned above, oil pressure is the result of the resistance of the oil to flow under a pumping action. Besides oil viscosity, changes in the oil galleries may also affect the resistance and thus the measured oil pressure. Smaller oil flow passages provide more resistance to oil flow, and therefore higher oil pressure and, conversely, large oil flow passages provide less resistance, resulting in lower oil pressure. For example, worn out bearings can result in low oil pressure. The procedure described in this section is applicable to different oil types and engine types. Wear in engine bearings during an oil change interval is presumed to be small and its effect on the oil pressure is negligible. However, the change over multiple oil change intervals can be large with no loss of accuracy.

In step 310 whether the vehicle engine is on is determined. This can be determined from a signal from the engine control module. The system does not proceed when the engine is not on or running. In step 312 whether the engine has recently had an oil change is determined. The reset 210 of FIG. 10 may be used to determine a reset. If there has been an oil change in step 312, whether the engine oil pressure is unregulated is determined in step 314. This may be determined by measuring the oil pressure and oil temperature by oil the temperature and pressure sensors located downstream of the oil filter illustrated in FIG. 2. When the oil flow is unregulated in step 314, the oil flow rate is directly related to the engine speed in step 316. The oil pressure and the engine RPM are measured and the oil viscosity indicator is calculated from Eqn. (3). In step 318 the viscosity and oil temperature are correlated. Adjustments may be made to the viscosity in view of the temperature. The fresh oil viscosity indicator, $\mu_{new}$, of the new oil is then registered or stored in a memory for future comparison with the used oil viscosity in step 320.

When the oil flow is regulated (not unregulated) in step 314, the correct oil flow is estimated from Eqn. (4) and the oil viscosity indicator is calculated from Eqn. (2) in step 322. Steps 318 and 320 are then also performed as describe above. It is also noted that the steps 314-320 are only performed after it has been determined that an oil change has taken place.

Referring back to step 312, when an oil change has not taken place, step 330 determines whether engine oil pressure is unregulated. This is accomplished by measuring the oil pressure and oil temperature using the engine temperature and pressure sensors. When it is determined that the oil flow is unregulated in step 330, the oil flow rate and engine speed are related in step 332 and thus the engine speed is used to determine the used oil viscosity indicator, $\mu_{old}$, by the same procedure as that described above for fresh oil in steps 316-318. Step 334 adjusts the viscosity for the oil temperature. When the used oil viscosity indicator, $\mu_{used}$, has been calculated in step 334, it is compared to the fresh oil viscosity, $\mu_{new}$, by, for example, forming a ratio by dividing $\mu_{used}$ by $\mu_{new}$ in step 336. In step 336 the ratio of viscosities is compared to a predetermined range defined by a lower constant $C_1$ and an upper constant $C_2$. The constants may be determined experimentally and depend on the oil properties. If the compared ratio value is outside the range defined by $C_1$ and $C_2$, an oil change signal is generated in step 338. A "change oil" warning signal may be sent to the vehicle operator when the viscosity estimated at a given oil temperature and engine speed exceeds a predetermined "threshold" or range as set forth above. In step 336 if the ratio is within the range in step 340, no oil change signal is generated since the viscosity is good.

Referring back to step 330, when the oil flow is regulated (not unregulated), the correct oil flow is estimated from Eqn. (4) and the oil viscosity indicator is calculated from Eqn. (2) in step 350. Steps 334 and 340 are then also performed as describe above.

Oil changes based on the present invention provide a means for achieving improved engine operational efficiency, more effective maintenance schedules, and extended engine life, all of which result in lower operational costs. In addition, the oil viscometer can protect against engine damage by warning the driver of sudden oil loss, or accelerated oil deterioration. Finally, oil changes based on the present disclosure may help to reduce the environmental cost of vehicle operation by extending the oil change interval.

Those skilled in the art can now appreciate from the foregoing description that the broad teachings of the present disclosure can be implemented in a variety of forms. Therefore, while this disclosure has been described in connection with particular examples thereof, the true scope of the disclosure should not be so limited since other modifications will become apparent to the skilled practitioner upon a study of the drawings, the specification and the following claims.

What is claimed is:

1. A method comprising:
   determining an engine oil pressure;
   determining an engine oil temperature;
   determining a viscosity of engine oil based on the engine oil pressure and the engine oil temperature when the engine oil pressure is regulated;
   comparing the viscosity of the engine oil to a threshold; and
   generating a warning signal in response to comparing the viscosity.

2. The method recited in claim 1 further comprising determining an engine speed and wherein determining the viscosity of the engine oil comprises determining the viscosity of the engine oil in response to the engine oil pressure, the engine oil temperature and the engine speed.

3. The method recited in claim 1 wherein comparing the viscosity of the engine oil comprises comparing the viscosity of the engine oil and a new engine oil viscosity to the threshold.

4. The method recited in claim 1 wherein comparing the viscosity of the engine oil comprises comparing a ratio of the viscosity of the engine oil and a new engine oil viscosity to a range threshold.

5. The method recited in claim 4 wherein generating the warning signal comprises generating the warning signal when the ratio is outside of the range threshold.

6. The method recited in claim 1 further comprising determining an unregulated oil flow range from the engine oil temperature and the engine oil pressure and wherein when an engine oil flow rate is in a regulated oil flow range, determining an oil flow rate based on the engine oil pressure, an engine speed and a regulated pressure.

7. The method recited in claim 6 wherein determining the viscosity of the engine oil comprises determining the viscosity of the engine oil from the oil flow rate and the engine oil pressure.

8. The method recited in claim 7, wherein determining the viscosity of the engine oil comprises determining the viscosity of the engine oil from the engine oil pressure, the engine oil temperature and the engine speed when the engine oil flow rate is in the regulated oil flow range.

9. A method comprising:
   determining a new oil viscosity;
   determining a used oil viscosity; and
   generating an indicator corresponding to oil life when a ratio of the used oil viscosity to the new oil viscosity is outside of a range, wherein at least one of the new oil viscosity and the used oil viscosity is determined when engine oil pressure is regulated.

10. The method recited in claim 9 further comprising indicating the oil is good when the ratio of the used oil viscosity to the new oil viscosity is within the range.

11. The method recited in claim 9 wherein determining the used oil viscosity comprises determining a used engine oil pressure, determining a used engine oil temperature, determining the used oil viscosity based on the used oil pressure and the used oil temperature.

12. The method recited in claim 9 wherein determining the used oil viscosity comprises determining a used engine oil pressure, determining a used engine oil temperature, determining an engine speed, and determining the used oil viscosity based on the used oil pressure, the engine speed and the used oil temperature.

13. The method recited in claim 12 further comprising determining an unregulated oil flow range from the used oil temperature and the used oil pressure and wherein when an engine oil flow is in a regulated oil flow range, determining a used oil flow rate based on the used oil pressure, the engine speed and a regulated pressure.

14. The method recited in claim 13 wherein determining the used oil viscosity comprises determining the used oil viscosity from the used oil flow rate and the used oil pressure.

15. The method recited in claim 13, wherein determining the used oil viscosity comprises determining the used oil viscosity from the used oil pressure, the used oil temperature and the engine speed when the engine oil flow is in the regulated oil flow range.

16. A control system for indicating engine oil life comprising:
   a viscosity determination module determining a viscosity of engine oil based on an engine oil pressure and engine oil temperature when the engine oil pressure is regulated; and
   a comparison module comparing the viscosity of the engine oil to a threshold and generating a warning signal in response to comparing the viscosity.

17. The control system recited in claim 16 wherein the viscosity determination module determines the viscosity of the engine oil based on the oil pressure, engine oil temperature and an engine speed.

18. The control system recited in claim 16 wherein the comparison module compares a ratio of the viscosity of the engine oil and a new oil viscosity to the threshold.

19. The control system recited in claim 16 further comprising an indicator receiving the warning signal and displaying an indicator of oil life.

20. The control system recited in claim 19 wherein the indicator of oil life comprises an oil change indicator.

* * * * *